United States Patent
Yi et al.

(10) Patent No.: US 11,313,982 B2
(45) Date of Patent: Apr. 26, 2022

(54) DIGITAL X-RAY DETECTOR AND METHOD FOR DRIVING THE SAME

(71) Applicant: LG Display Co., Ltd., Seoul (KR)

(72) Inventors: Youngjin Yi, Seoul (KR); Siu Yoon, Goyang-si (KR)

(73) Assignee: LG DISPLAY CO., LTD., Seoul (KR)

( * ) Notice: Subject to any disclaimer, the term of this patent is extended or adjusted under 35 U.S.C. 154(b) by 51 days.

(21) Appl. No.: 16/726,691

(22) Filed: Dec. 24, 2019

(65) Prior Publication Data

US 2020/0209416 A1 Jul. 2, 2020

(30) Foreign Application Priority Data

Dec. 28, 2018 (KR) ........................ 10-2018-0172376

(51) Int. Cl.
| | |
|---|---|
| *G01T 1/24* | (2006.01) |
| *H01L 27/146* | (2006.01) |
| *A61B 6/00* | (2006.01) |
| *H04N 5/32* | (2006.01) |

(52) U.S. Cl.
CPC ............ *G01T 1/247* (2013.01); *A61B 6/4233* (2013.01); *H01L 27/14676* (2013.01); *H04N 5/32* (2013.01)

(58) Field of Classification Search
None
See application file for complete search history.

(56) References Cited

U.S. PATENT DOCUMENTS

| | | | |
|---|---|---|---|
| 2012/0287320 A1* | 11/2012 | Shah ..................... | H04N 5/378 348/300 |
| 2013/0194118 A1* | 8/2013 | Coln .................... | H04N 5/3575 341/155 |

FOREIGN PATENT DOCUMENTS

| | | | | |
|---|---|---|---|---|
| EP | 1349379 A2 * | 10/2003 | ............. | H04N 5/361 |
| KR | 10-1745436 B1 | 6/2017 | | |
| KR | 10-2016-0078602 A | 7/2018 | | |
| KR | 10-2018-0078603 A | 7/2018 | | |

* cited by examiner

*Primary Examiner* — Edwin C Gunberg
(74) *Attorney, Agent, or Firm* — Polsinelli PC

(57) ABSTRACT

A digital X-ray detector comprises a pixel array including a plurality of pixel regions; and a data line; and a read-out driver connected to the data line, wherein each pixel region includes a photo-sensing element and a pixel switch disposed between the photo-sensing element and the data line, wherein the read-out driver includes: an amplification unit connected to each data line; a first association signal detector connected to an output of the amplification unit and detecting a first association signal corresponding to an offset of the amplification unit; a second association signal detector connected to the output of the amplification unit and detecting a second association signal including an output signal of the photo-sensing element; and a third association signal detector connected to the output of the amplification unit and detecting a third association signal corresponding to an offset of the pixel region.

22 Claims, 10 Drawing Sheets

DIGITAL X-RAY DETECTOR AND METHOD FOR DRIVING THE SAME

CROSS REFERENCE TO RELATED APPLICATION

This application claims the priority of Korean Patent Application No. 10-2018-0172376 filed on Dec. 28, 2018, which is hereby incorporated by reference in its entirety.

BACKGROUND

Field of the Disclosure

The present disclosure relates to a digital X-ray detector (DXD) for detecting a transmission of X-rays and a method for driving the detector.

Description of the Background

X-ray is an electromagnetic wave having permeability. A transmission of the X-ray corresponds to a density inside an object. Therefore, a X-ray image is widely used in medical, security and industrial fields. In particular, the X-ray image is frequently used as a basic diagnostic tool in the medical field.

A conventional X-ray image is realized by providing a film made of a photosensitive material, exposing the film to an X-ray transmitting the object, and then transferring an image of the film to a printing paper. In this case, there is a problem that the image information cannot be provided in real time due to a printing process, and the image information may be easily lost due to inability to store the film for a long time.

In recent years, due to development of video processing technology and semiconductor technology, a digital X-ray detector with a flat panel structure that may replace the film has been proposed.

A typical digital X-ray detector includes a pixel array including a plurality of photo-sensing elements corresponding to a plurality of pixel regions arranged in a sensing region, and a read-out driver that reads out the sensing signal from a photo-sensing device of each pixel region. In this connection, the photo sensing device includes a photo-reaction part which generates electrons in response to incident light amount, thereby outputting a sensing signal corresponding to the light. Then, the read-out driver derives a plurality of sensing signals corresponding to the plurality of pixel regions, and generates an image signal based on the plurality of sensing signals. As a result, the digital X-ray detector provides the X-ray image.

However, in the process of the read-out driver reading-out the sensing signal of each pixel region, an offset of the pixel array and an offset of the read-out driver may be read out together with the sensing signal of each pixel region. As a result, accuracy and reliability of the X-ray image provided by the digital X-ray detector may be degraded.

SUMMARY

The present disclosure provides a digital X-ray detector that can improve the accuracy and reliability of the X-ray image and a method for driving the detector.

The present disclosure is not limited to the above-mentioned aspect. Other advantages of the present disclosure as not mentioned above may be understood from following descriptions and more clearly understood from aspects of the present disclosure. Further, it will be readily appreciated that the purposes and advantages of the present disclosure may be realized by features and combinations thereof as disclosed in the claims.

In a first aspect of the present disclosure, there is proposed a digital X-ray detector comprising: a pixel array: including a plurality of pixel regions arranged in a matrix in a sensing region; and a data line corresponding to pixel regions arranged in a direction among the plurality of pixel regions; and a read-out driver connected to the data line, wherein each pixel region includes a photo-sensing element sensing light and a pixel switch disposed between the photo-sensing element and the data line, wherein the read-out driver includes: an amplification unit connected to each data line; a first association signal detector connected to an output of the amplification unit and detecting a first association signal corresponding to an offset of the amplification unit; a second association signal detector connected to the output of the amplification unit and detecting a second association signal including an output signal of the photo-sensing element; a third association signal detector connected to the output of the amplification unit and detecting a third association signal corresponding to an offset of the pixel region; and a multiplexer deriving a sensing signal of each pixel region based on the first, second and third association signals.

In one implementation of the first aspect, the multiplexer subtracts the first and third association signals from the second association signal to obtain a subtraction result and derives the subtraction result as the sensing signal.

In one implementation of the first aspect, the first association signal detector includes: a first buffer capacitor charged based on the first association signal; and a first buffer switch disposed between the amplification unit and the first buffer capacitor, wherein the second association signal detector includes: a second buffer capacitor charged based on the second association signal; and a second buffer switch disposed between the amplification unit and the second buffer capacitor, wherein the third association signal detector includes: a third buffer capacitor charged based on the third association signal; and a third buffer switch disposed between the amplification unit and the third buffer capacitor.

In one implementation of the first aspect, during a portion of an idle period before termination of the idle period prior to irradiation of X-ray to the plurality of pixel regions, the pixel switch is turned on and off, and then the third buffer switch is turned on, wherein a pixel offset signal including the offset of the pixel region is transmitted to the data line via the pixel switch as turned on, wherein the third association signal corresponding to the pixel offset signal is transmitted to the third buffer capacitor via the third buffer switch as turned on.

In one implementation of the first aspect, during a detection period after the X-ray irradiation to the plurality of pixel regions, the first buffer switch is turned on, such that the first association signal is transmitted to the first buffer capacitor via the first buffer switch as turned on, wherein after the first buffer switch is turned off, the pixel switch is turned on, such that a pixel signal including the offset of the pixel region and the output signal of the photo-sensing element is transmitted to the data line via the pixel switch as turned on, wherein after the pixel switch is turned off, the second buffer switch is turned on, such that the second association signal including the pixel signal and the offset of the amplification unit is transmitted to the second buffer capacitor via the second buffer switch as turned on.

In one implementation of the first aspect, during a detection period after the X-ray irradiation to the plurality of pixel regions, the first buffer switch is turned on, such that the first association signal is transmitted to the first buffer capacitor via the first buffer switch as turned on, wherein after the first buffer switch is turned off, the pixel switch is first turned on, such that the pixel signal including the offset of the pixel region and the output signal of the photo-sensing element is transmitted to the data line via the pixel switch as turned on, wherein after the pixel switch is first turned off, the second buffer switch is turned on, such that the second association signal including the pixel signal and the offset of the amplification unit is transmitted to the second buffer capacitor via the second buffer switch as turned on, wherein after the second buffer switch is turned off, the pixel switch is second turned on, such that a pixel offset signal including the offset of the pixel region is transmitted to the data line via the pixel switch as turned on, wherein after the pixel switch is second turned off, the third buffer switch is turned on, such that the third association signal corresponding to the pixel offset signal is transmitted to the third buffer capacitor via the third buffer switch as turned on.

In one implementation of the first aspect, a length of an elapsed time from a time point when the pixel switch is first turned off to a time point when the pixel switch is second turned on is equal to a length of an elapsed time from a time point when the X-ray irradiation to the plurality of pixel regions terminates to a time point when the pixel switch is first turned on.

In one implementation of the first aspect, the amplification unit includes: an amplifier including a first input connected to the data line and a second input receiving a predetermined reference signal; and a feedback capacitor disposed between the first input and an output of the amplifier.

In one implementation of the first aspect, the multiplexer combines sensing signals of the pixel regions with each other to generate an analog output signal, wherein the read-out driver includes: a signal converter for converting the analog output signal into a digital output signal; and a data processing unit for generating an image signal based on the digital output signal.

In a second aspect of the present disclosure, there is proposed a method for operating a digital X-ray detector, wherein the digital X-ray detector includes: a pixel array: including a plurality of pixel regions arranged in a matrix in a sensing region; and a data line corresponding to each vertical line composed of pixel regions arranged in a vertical direction among the plurality of pixel regions; and a read-out driver connected to the data line, wherein each pixel region includes a photo-sensing element for sensing light, and a pixel switch disposed between the photo-sensing element and the data line, wherein the read-out driver includes: an amplification unit coupled to each data line; first, second, and third buffer capacitors coupled to an output of the amplification unit; first, second, and third buffer switches disposed between the first, second, and third buffer capacitors and the output of the amplification unit respectively; and a multiplexer connected to the first, second, and third buffer capacitors, wherein the method comprises: turning on the first buffer switch during a first period of a detection period after irradiating X-ray to the plurality of pixel regions; turning on the pixel switch during a second period of the detection period; turning on the second buffer switch during a third period of the detection period; and deriving, by the multiplexer, a sensing signal of each pixel region, based on first, second and third association signals corresponding to the first, second and third buffer capacitors respectively.

In one implementation of the second aspect, when the first buffer switch is turned on, the first association signal corresponding to an offset of the amplification unit is transmitted to the first buffer capacitor via the first buffer switch as turned on, wherein when the pixel switch is turned on, a pixel signal including an offset of the pixel region and an output signal of the photo-sensing element is transmitted to the data line via the pixel switch as turned on, wherein when the second buffer switch is turned on, the second association signal including the pixel signal and the offset of the amplification unit is transmitted to the second buffer capacitor via the second buffer switch as turned on.

In one implementation of the second aspect, the method further comprises, during a portion of an idle period before termination of the idle period prior to irradiation of X-ray to the plurality of pixel regions, turning on and off the pixel switch, and turning on the third buffer switch, wherein during the portion of the idle period, a pixel offset signal including the offset of the pixel region is transmitted to the data line via the pixel switch as turned on, wherein during the portion of the idle period, the third association signal corresponding to the pixel offset signal is transmitted to the third buffer capacitor via the third buffer switch as turned on.

In one implementation of the second aspect, the method further comprises: during a fourth period after the third period of the detection period, turning on the pixel switch such that the third association signal corresponding to an offset of the pixel region is transmitted to the data line via the pixel switch as turned on; and during a fifth period after the fourth period of the detection period, turning on the third buffer switch such that the third associated signal is transmitted to the third buffer capacitor via the third buffer switch as turned on.

In one implementation of the second aspect, a length of the third period is equal to a length of the first period.

In one implementation of the second aspect, deriving, by the multiplexer, the sensing signal of each pixel region includes: subtracting, by the multiplexer, the first and third association signals from the second association signal to obtain a subtraction result; and deriving, by the multiplexer, the subtraction result as the sensing signal.

In a third aspect of the present disclosure, there is proposed a digital X-ray detector including a photo-sensing element and a pixel switch corresponding to each pixel region, a data line corresponding to each vertical line, an amplification unit connected to each data line, a first association signal detector for detecting a first association signal corresponding to the offset of the amplification unit, a second association signal detector for detecting a second association signal including a sensing signal from the photo-sensing element, a third association signal detector for detecting a third association signal corresponding to an offset of the pixel region, and a multiplexer for deriving a sensing signal of each pixel region based on the first, second and third association signals.

In this connection, the multiplexer may derive the sensing signal of each pixel region based on the first and third association signals corresponding to the offset of the amplification unit and the offset of the pixel region along with the second association signal that includes the output signal of the photo-sensing element.

That is, including the first and third association signal detectors may allow the multiplexer to remove the offset of the amplification unit and the offset of the pixel region to derive the sensing signal of each pixel region. Therefore, the sensing signal of each pixel region derived by the multiplexer may be more substantially similar to the output signal of the photo-sensing element corresponding to the X-ray transmission.

When an image signal generated based on such a sensing signal is provided as an X-ray image, the influence of the offset of the digital X-ray detector itself on the X-ray image can be minimized, such that the accuracy and reliability of the X-ray image may be improved.

BRIEF DESCRIPTION OF THE DRAWINGS

The accompanying drawings, which are included to provide a further understanding of the disclosure and are incorporated in and constitute a part of the disclosure, illustrate aspects of the disclosure and together with the description serve to explain the principle of the disclosure.

In the drawings.

DETAILED DESCRIPTIONS

Figure 1:
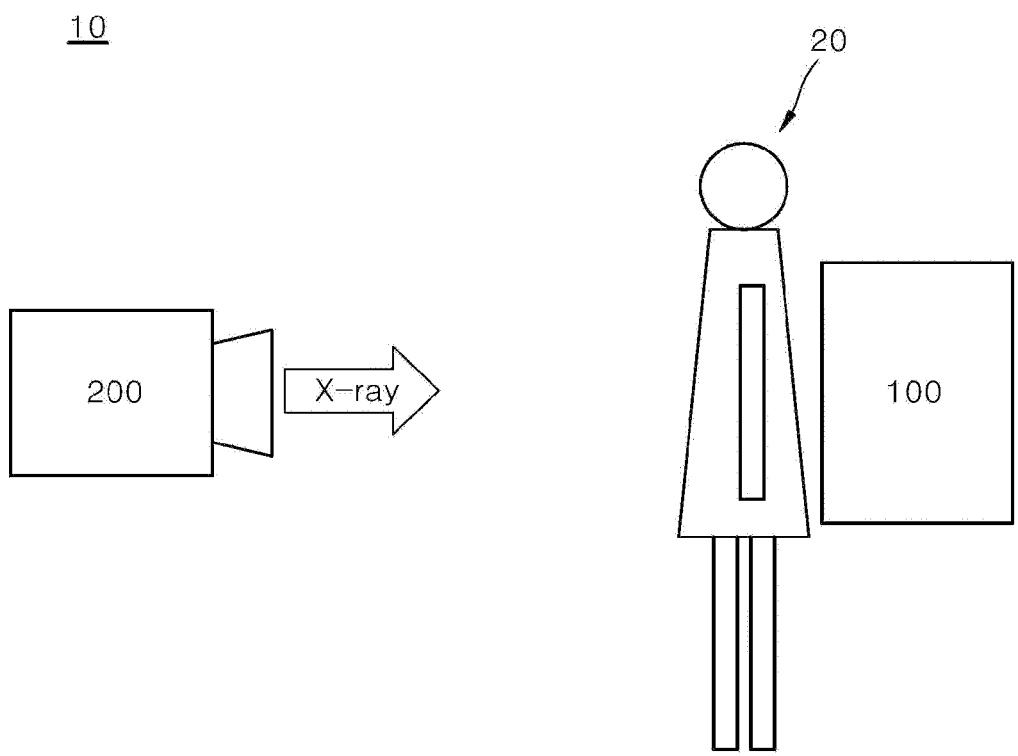
FIG. 1 shows an X-ray image system according to an aspect of the present disclosure.

For simplicity and clarity of illustration, elements in the figures are not necessarily drawn to scale. The same reference numbers in different figures denote the same or similar elements, and as such perform similar functionality. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various aspects are illustrated and described further below. It will be understood that the description herein is not intended to limit the claims to the specific aspects described. On the contrary, it is intended to cover alternatives, modifications, and equivalents as may be included within the spirit and scope of the present disclosure as defined by the appended claims.

The terminology used herein is for the purpose of describing particular aspects only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a digital X-ray detector and a method for driving the detector according to each aspect of the present disclosure will be described in detail with reference to the accompanying drawings.

First, referring to FIGS. 1 to 3, a digital X-ray detector and an X-ray imaging system including the digital X-ray detector according to an aspect of the present disclosure will be described.

FIG. 1 shows an X-ray image system according to an aspect of the present disclosure. FIG. 2 shows a digital X-ray detector in FIG. 1. FIG. 3 shows a pixel region of a pixel array and a read-out driver in FIG. 2.

As shown in FIG. 1, an X-ray imaging system 10 is configured to provide an X-ray image of an interior of a predetermined target object 20. In one example, the target object 20 may be a part of a living body to be tested or a part of an industrial process product to be inspected.

The X-ray imaging system 10 includes a digital X-ray detector 100 for detecting a transmission of an X-ray, and a light-source device 200 which faces away the digital X-ray detector 100 with the target object 20 therebetween and irradiates the X-ray to the target object 20.

The digital X-ray detector 100 may be embodied as a form of a flat panel including a sensing region for detecting the X-ray transmission through the target object 20.

Figure 2:
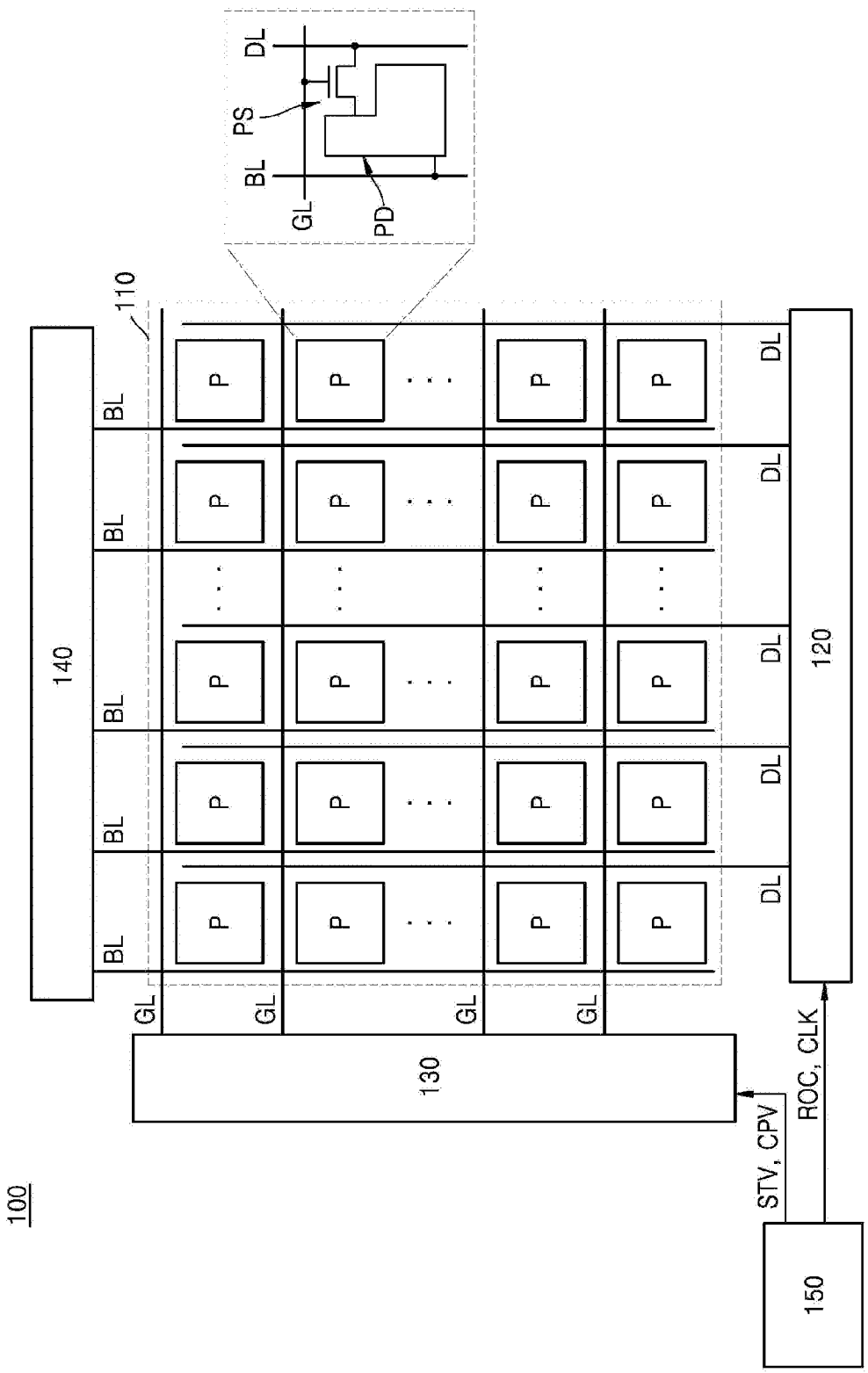
FIG. 2 shows a digital X-ray detector in FIG. 1.

As shown in FIG. 2, the digital X-ray detector 100 includes a pixel array 110 including a plurality of pixel regions P arranged in a matrix in a sensing region, and a read-out driver 120 connected to a data line DL of the pixel array 110.

The digital X-ray detector 100 further includes a gate driver 130 connected to a gate line GL of the pixel array 110, a bias driver 140 connected to a bias line BL of the pixel array 110, and a timing controller 150 for controlling a driving timing of the data driver 120 and the gate driver 130.

Each pixel region P of the pixel array 110 includes a photo-sensing element PD (PIN diode) for sensing light, and a pixel switch PS disposed between the photo-sensing element PD and the data line DL. Although not shown separately, the pixel array 110 may further include a scintillator layer (not shown) that converts the X-ray to visible light.

When the pixel switch PS is turned on based on a gate signal from the gate line GL, the pixel switch transfers an output signal of the photo-sensing element PD to the data line DL.

The scintillator layer converts the X-ray to visible light.

The photo-sensing element PD absorbs the visible light from the scintillator layer and generates electrons in response to the visible light, thereby to generate an output signal corresponding to the transmission of the X-ray.

The timing controller 150 supplies a start signal STV and a clock signal CPV for controlling the driving timing of the gate driver 130 to the gate driver 130. Then, the timing controller 150 supplies a read-out control signal ROC and a read-out clock signal CLK for controlling driving timing of the read-out driver 120 to the data driver 120.

The gate driver 130 sequentially supplies a gate signal for turning on the pixel switch PS included in each horizontal line to each gate line GL. In this connection, each horizontal line is composed of pixel regions P arranged horizontally (in a left-right direction in FIG. 2) among the plurality of pixel regions P. The gate line GL of the pixel array 110 may correspond to each horizontal line.

The bias driver 140 supplies the bias line BL with a bias signal for applying a predetermined bias voltage to the photo-sensing element PD. In this connection, the bias driver 140 may selectively supply a bias signal for a reverse bias operation or a bias signal for a forward bias operation.

The read-out driver 120 receives the output signal of the photo-sensing element PD of each pixel region P of each horizontal line through the data line DL, and generates an image signal based on the received signal.

As shown in FIG. 2, the data line DL and the bias line BL may correspond to each vertical line. Each vertical line is composed of pixel regions P arranged in a vertical direction (in an up-down direction in FIG. 2) among the plurality of pixel regions P.

Figure 3:
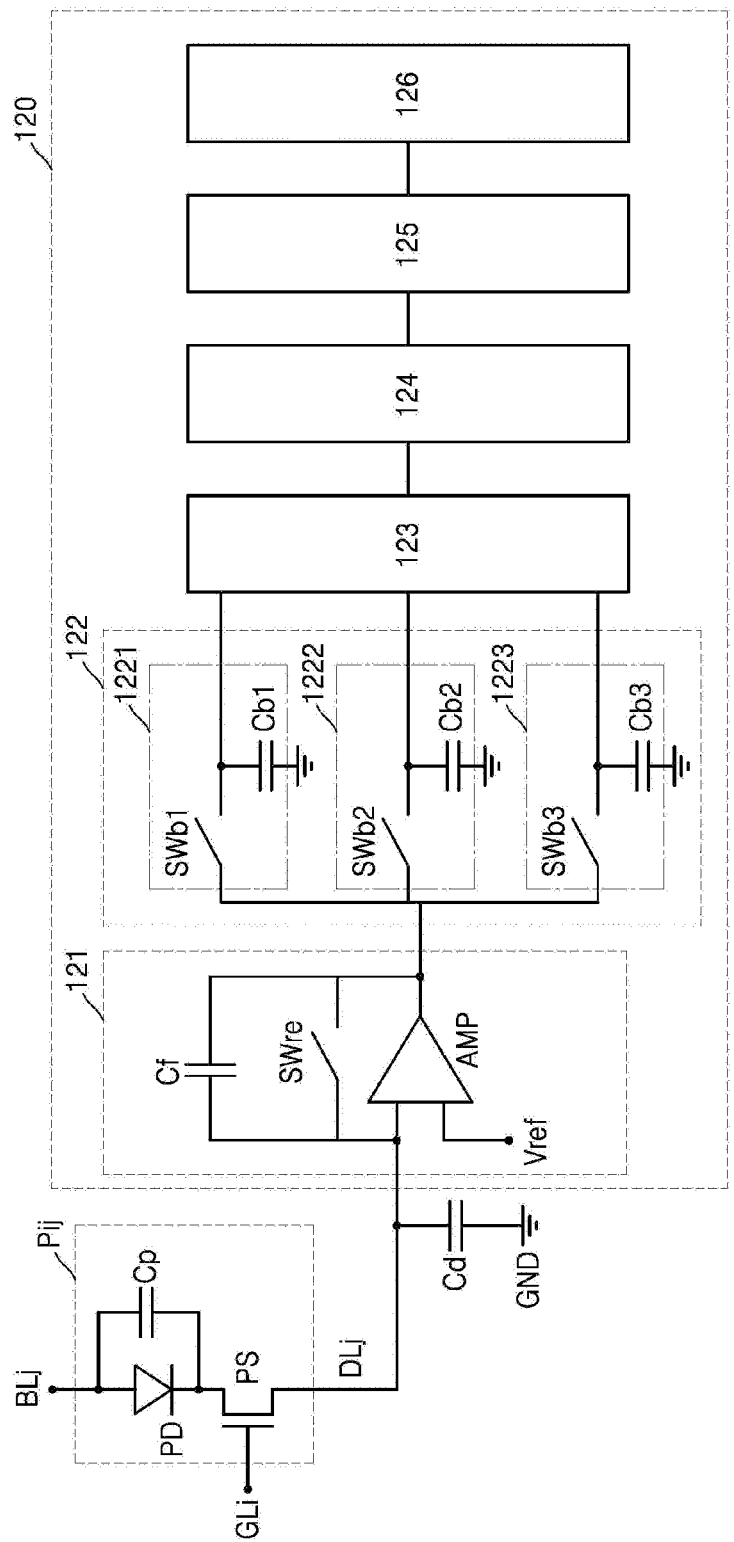
FIG. 3 shows a pixel region of a pixel array and a read-out driver in FIG. 2.

As shown in FIG. 3, one pixel region Pij of the plurality of pixel regions P may be connected to an i-th gate line GLi corresponding to an i-th horizontal line, and to a j-th data line DLj and a j-bias line BLj corresponding to a j-th vertical line.

For example, the pixel region Pij includes the photo-sensing element PD for sensing light, and the pixel switch PS arranged between the photo-sensing element PD and the data line DLj.

In one example, an anode of the photo-sensing element PD may be connected to the bias line BLj, while a cathode of the photo-sensing element PD may be connected to the pixel switch PS.

The photo-sensing element PD includes a semiconductor layer that reacts with the visible light from the scintillator layer to produce electron-hole pairs. In this photo-sensing element PD, the electron of the electron-hole pair moves to the cathode due to the bias signal of the bias line BL supplied to the anode. At this time, an output signal corresponding to the X-ray transmission is generated based on the amount of electrons being moved.

When the pixel switch PS is turned on based on the gate signal of the gate line GLi, the switch connects the photo-sensing element PD to the data line DLj.

Any pixel region Pij may further include a pixel capacitor Cp connected in parallel with the photo-sensing element PD. In this connection, the pixel capacitor Cp is charged based on the output signal of the photo-sensing element PD. When the pixel switch PS is turned on, the pixel capacitor Cp transfers the charged signal to the data line DLj.

The pixel array 110 may further include a data capacitor Cd connected to each data line DLj. The data capacitor Cd is charged with a signal transmitted to the data line DLj.

The read-out driver 120 includes an amplification unit 121 connected to each data line DLj, a signal buffering unit 122 connected to an output of the amplification unit 121 and containing first, second and third association signals, and a multiplexer 123 for deriving a sensing signal of each pixel region based on the first, second and third association signals.

The amplification unit 121 may include an amplifier AMP including a first input connected to each data line DLj and a second input for receiving a predetermined reference signal Vref, and a feedback capacitor Cf disposed between the first input and an output of the amplifier AMP.

The amplifier AMP amplifies a signal of the first input, that is, a signal of the data line DLj based on the reference signal Vref and a capacitance of the feedback capacitor Cf, and outputs the amplified signal to the output. The capacitance of the feedback capacitor Cf corresponds to a gain of the amplifier AMP.

The amplification unit 121 may further include a reset switch SWre connected in parallel with the feedback capacitor Cf.

The reset switch SWre is configured to initialize the feedback capacitor Cf. In one example, before irradiating an X-ray to the plurality of pixel regions P, an initialization period may be defined. During the initialization period, all of the reset switches SWre of the amplification units 121 corresponding to all of the data lines DL may be turned on.

The signal buffering unit 122 includes first, second and third association signal detectors 1221, 1222 and 1223 connected to the output of the amplifier AMP and configured for detecting first, second and third association signals respectively.

The first association signal corresponds to an offset of the amplification unit 121. The offset of the amplification unit 121 may correspond to parasitic capacitance or leakage current due to the amplifier AMP.

The second association signal includes an output signal of the photo-sensing element PD.

The third association signal corresponds to an offset of the pixel region P. In this connection, the offset of the pixel region P corresponds to the charges accumulated in the photo-sensing element PD or the pixel capacitor Cp of each pixel region P due to leakage current or the like. In particular, an offset of the pixel switch PS may correspond to a leakage current occurring during a period from an end of irradiation of the X-ray to a turn-on timing of the pixel switch PS.

The first association signal detector 1221 includes a first buffer capacitor Cb1 that is charged based on the first association signal, and a first buffer switch SWb1 that is disposed between the amplification unit 121 and the first buffer capacitor Cb1.

The first association signal transmitted to the first buffer capacitor Cb1 may correspond to a voltage of the output of the amplifier AMP before a signal of the data line DLj is applied to the first input of the amplifier AMP.

The second association signal detector 1222 includes a second buffer capacitor Cb2 that is charged based on the second association signal, and a second buffer switch SWb2 that is disposed between the amplification unit 121 and the second buffer capacitor Cb2.

In this connection, the second association signal transmitted to the second buffer capacitor Cb2 includes an output signal of the photo-sensing element PD, an offset of the pixel region P, and an offset of the amplification unit 121.

The third association signal detector 1223 includes a third buffer capacitor Cb3 that is charged based on the third association signal, and a third buffer switch SWb3 that is disposed between the amplification unit 121 and the third buffer capacitor Cb3.

The third association signal transmitted to the third buffer capacitor Cb3 corresponds to a reverse bias data of the pixel region P due to the leakage current, that is, to the offset of the pixel region P. That is, the third association signal corresponds to the offset of the pixel region P included in the second association signal.

The multiplexer 123 derives a sensing signal of each pixel region P based on the first, second and third association signals. That is, the multiplexer 123 may derive the sensing signal of each pixel region P by subtracting the first and third association signals from the second association signal.

Thus, the sensing signal of each pixel region P derived by the multiplexer 123 is not affected by the offset of the amplification unit 121 corresponding to the first association signal and the offset of the pixel region P corresponding to the third association signal.

Accordingly, the sensing signal of each pixel region P derived by the multiplexer 123 may be substantially equal to the output signal of the photo-sensing element PD of each pixel region P. That is, when the sensing signal is derived by the multiplexer 123, the accuracy and reliability of the X-ray image may be improved.

The multiplexer 123 combines the sensing signals of the pixel regions to generate an analog output signal.

Further, the read-out driver 120 may further include a signal conversion unit 124 for converting the analog output signal of the multiplexer 123 into a digital output signal, and a data processing unit 125 for generating an image signal based on the digital output signal. In this connection, the image signal may be a signal representing a luminance value corresponding to each of the plurality of pixel regions P as bit information.

The read-out driver 120 may further include a communication unit 126 for transferring the image signal to a display (not shown) using a predetermined communication scheme. For example, the communication unit 126 may be composed of a CMOS integrated circuit for transmitting/receiving a signal using an LVDS (low-voltage differential signaling) scheme.

Next, a driving method of the digital X-ray detector 100 according to an aspect of the present disclosure will be described with reference to FIGS. 4 to 9.

Figure 4:
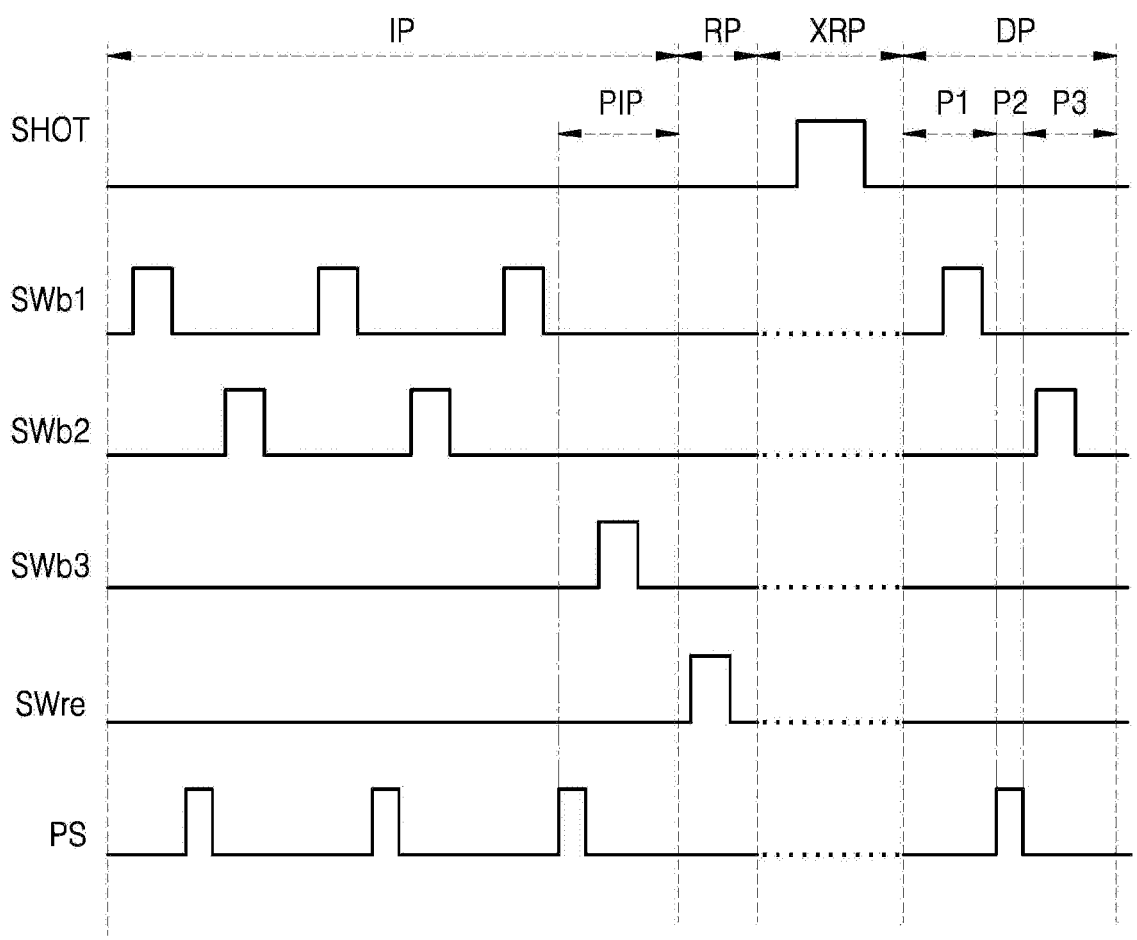
FIG. 4 shows a driving waveform corresponding to the pixel region and the read-out driver of FIG. 3 according to an aspect of the present disclosure.

FIG. 4 shows a driving waveform corresponding to the pixel region and the read-out driver of FIG. 3 according to an aspect of the present disclosure.

Figure 5:
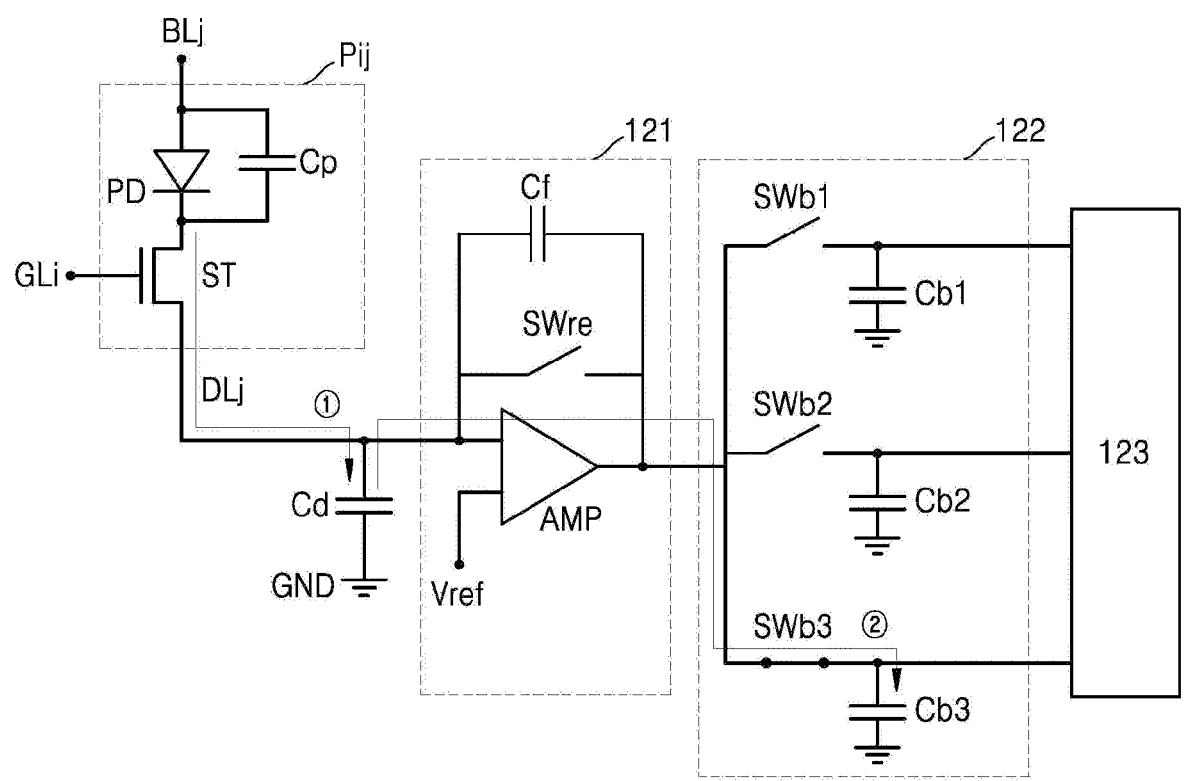
FIG. 5 shows an operation of the pixel region and the read-out driver in FIG. 3, corresponding to a portion of an idle period of FIG. 4.
Figure 6:
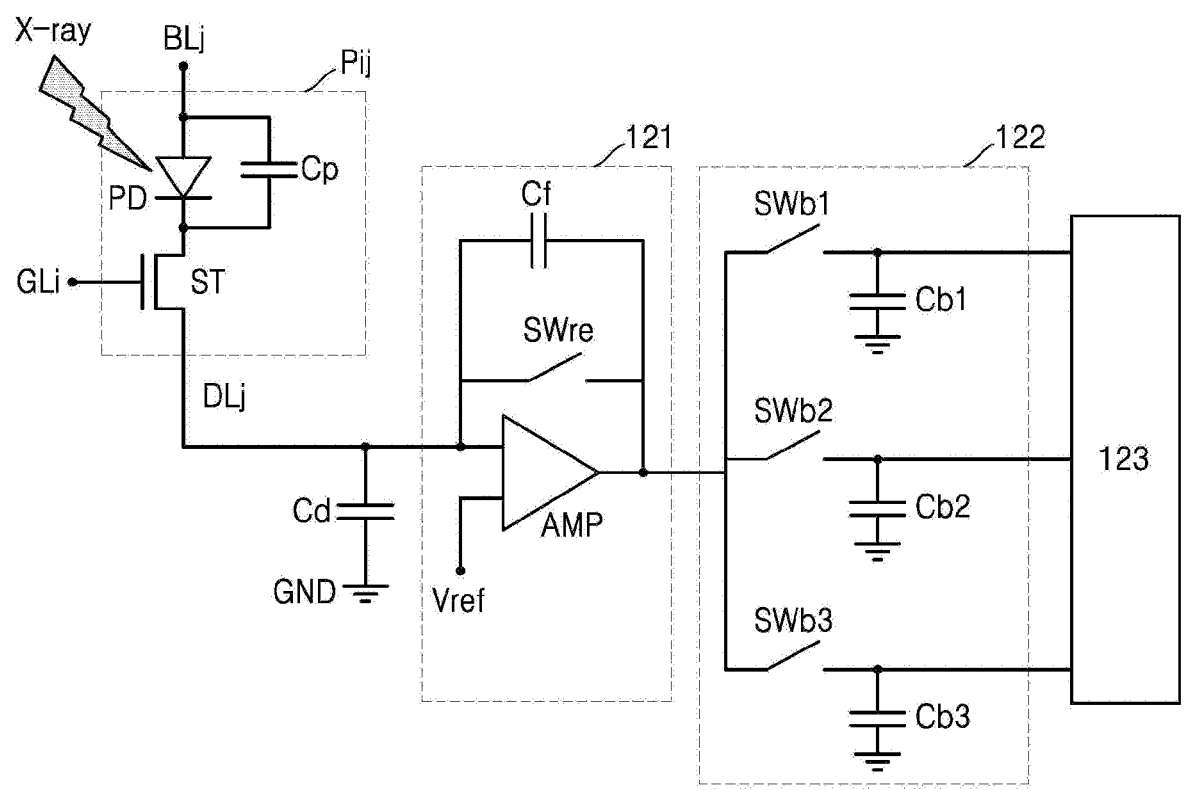
FIG. 6 shows an operation of the pixel region and the read-out driver in FIG. 3, corresponding to an radiation period of FIG. 4.
Figure 7:
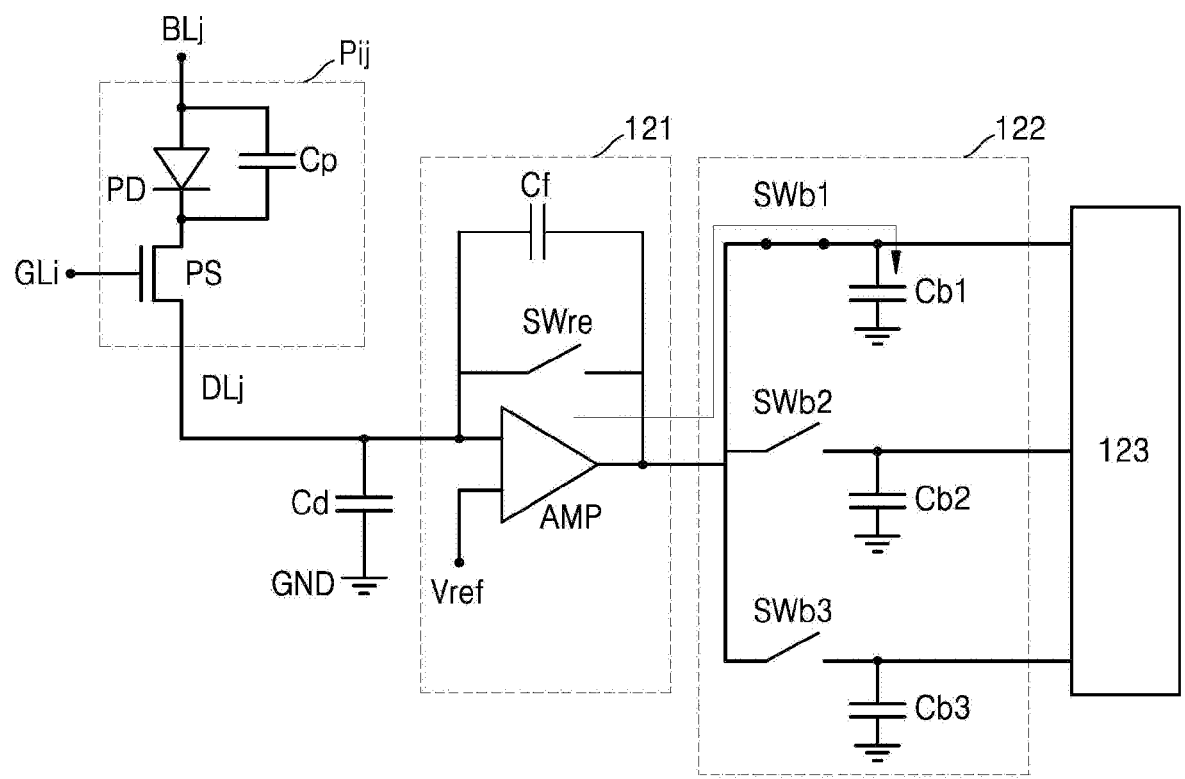
FIG. 7 shows an operation of the pixel region and the read-out driver in FIG. 3, corresponding to a first period of a detection period of FIG. 4.
Figure 8:
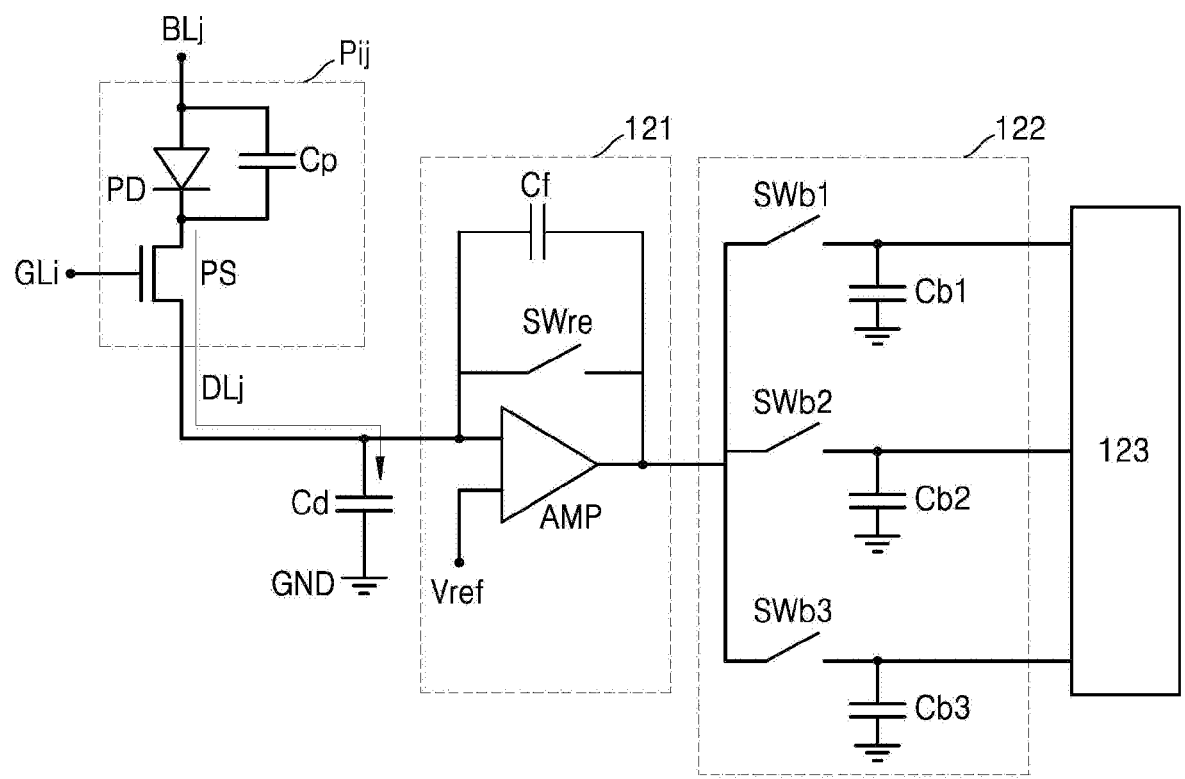
FIG. 8 shows an operation of the pixel region and the read-out driver in FIG. 3, corresponding to a second period of a detection period of FIG. 4.
Figure 9:
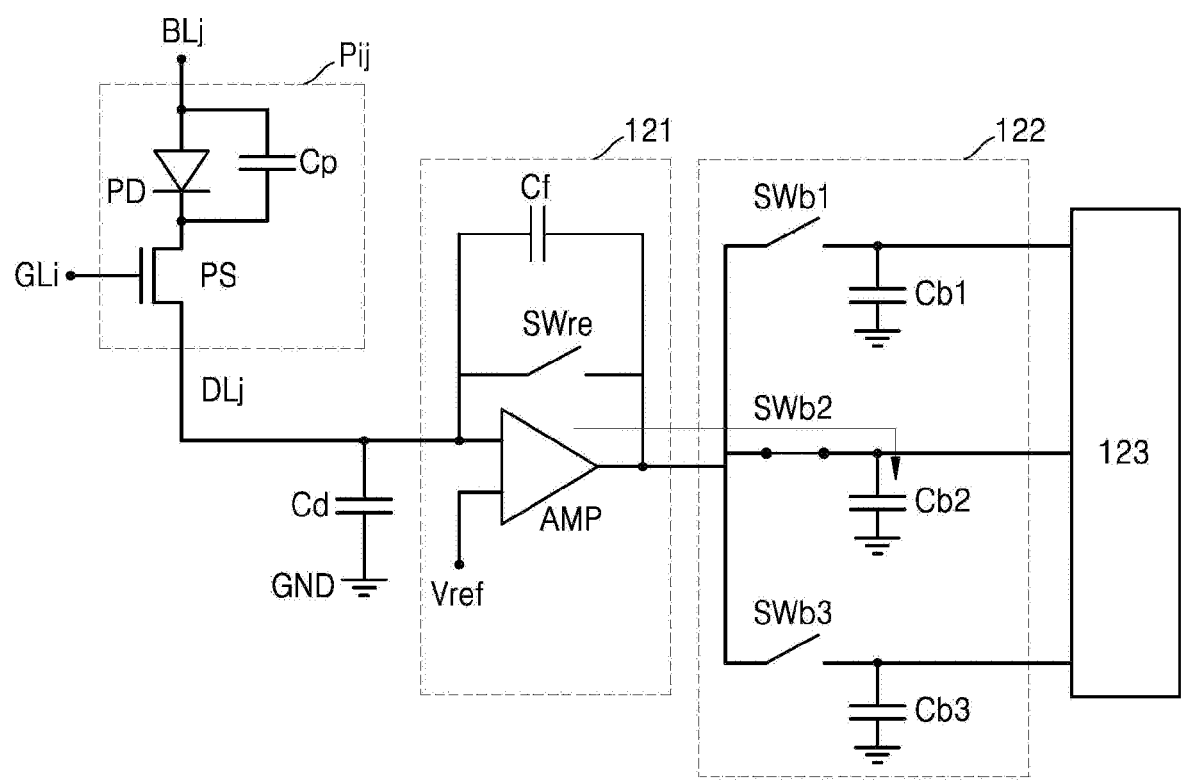
FIG. 9 shows an operation of the pixel region and the read-out driver in FIG. 3, corresponding to a third period of a detection period of FIG. 4.

FIG. 5 shows an operation of the pixel region and the read-out driver in FIG. 3, corresponding to a portion of an idle period of FIG. 4. FIG. 6 shows an operation of the pixel region and the read-out driver in FIG. 3, corresponding to a radiation period of FIG. 4. FIG. 7 shows an operation of the pixel region and the read-out driver in FIG. 3, corresponding to a first period of a detection period of FIG. 4. FIG. 8 shows an operation of the pixel region and the read-out driver in FIG. 3, corresponding to a second period of a detection period of FIG. 4. FIG. 9 shows an operation of the pixel region and the read-out driver in FIG. 3, corresponding to a third period of a detection period of FIG. 4.

As shown in FIG. 4, the first and second buffer switches SWb1 and SWb2 and the pixel switch PS are alternately turned on and off during an idle period IP prior to a radiation period XRP for irradiating the X-ray to the plurality of pixel regions P. In this connection, the number of times that the first and second buffer switches SWb1 and SWb2 and the pixel switch PS are turned on may be at least once.

During the idle period IP, all of the pixel switches PS of all of the pixel regions P may be turned on and off at the same time. Alternatively, during the idle period IP, the pixel switches PS of at least one horizontal line may be turned on and off sequentially.

Thus, before the digital X-ray detector 100 detects the X-ray transmission, the charges accumulated on the photo-sensing element PD of each pixel region PD due to noise light or leakage current may be removed. This may improve the accuracy of the X-ray image.

During a portion (PIP: portion of IP) of the IP before the IP termination, the pixel switch PS turns on and off, and the third buffer switch SWb3 turns on.

In this connection, as shown in a first path ① in FIG. 5, a pixel offset signal including the offset of each pixel region P is transmitted to the data line DLj through the pixel switch PS as turned on. In this connection, the data capacitor Cd is charged with the pixel offset signal.

The offset of each pixel region P corresponds to the charges accumulated in the photo-sensing element PD or the pixel capacitor Cp of each pixel region PD due to leakage current or the like.

Further, the amplifier AMP outputs the third association signal corresponding to the pixel offset signal.

Then, as shown in a second path ② in FIG. 5, the third association signal corresponding to the pixel offset signal is transmitted to the third buffer capacitor Cb3 through the third buffer switch SWb3 that is turned on. Thus, the third buffer capacitor Cb3 is charged with the third association signal.

In this connection, each third buffer capacitor Cb3 corresponding to each data line DL may be charged with the third association signal corresponding to the offset of the pixel region P included in at least one horizontal line.

In one example, the third association signal transmitted to the third buffer capacitor Cb3 may correspond to an average value of offsets of the pixel regions P included in all of the horizontal lines.

Alternatively, the third association signal transmitted to the third buffer capacitor Cb3 may correspond to the lowest or highest offset value among the offsets of the pixel regions P included in all of the horizontal lines.

Alternatively, the third association signal transmitted to the third buffer capacitor Cb3 may correspond to an average value of offsets of the pixel regions P included in a representative horizontal line of each block. In this connection, each block may be composed of two or more consecutive horizontal lines. All of the horizontal lines may be divided into a plurality of blocks.

Alternatively, the third association signal transmitted to the third buffer capacitor Cb3 may correspond to an average value of offsets of the pixel regions P included in two or more horizontal lines corresponding to one block.

As such, the third association signal transmitted to the third buffer capacitor Cb3 during the portion PIP of the idle period IP may be set to any value as long as the value reflects the offset of the pixel region P included in at least one horizontal line.

Then, as shown in FIG. 4, during a reset period RP after the end of the idle period IP and just before the radiation period XRP, the reset switch SWre turns on. In this connection, the feedback capacitor Cf of the amplification unit 121 is reset.

During the radiation period XRP, emission SHOT of the X-ray to the pixel array 110 is performed.

Thus, as shown in FIG. 6, since the pixel array 110 of the digital X-ray detector 100 is exposed to the X-ray, the photo-sensing element PD of each pixel region P generates an output signal corresponding to the transmission.

As shown in FIG. 4, a detection period DP after the radiation period XRP includes first, second and third periods P1, P2 and P3.

During the first period P1 of the detection period DP, the first buffer switch SWb1 is turned on.

During the second period P2 of the detection period PD, the pixel switch PS is turned on.

During the third period P3 of the detection period PD, the second buffer switch SWb2 is turned on.

As shown in FIG. 7, when the first buffer switch SWb1 is turned on during the first period P1 of the detection period DP, The first association signal corresponding to the offset of the amplifier 121 is transmitted to the first buffer capacitor Cb1 through the first buffer switch SWb1 that is turned on. Thus, the first buffer capacitor Cb1 is charged with the first association signal.

In this connection, the first association signal includes the output of the amplifier AMP irrespective of the signal of the data line DLj.

As shown in FIG. 8, when the pixel switch PS is turned on during the second period P2 of the detection period DP, a pixel signal including the offset of the pixel region P and the output signal of the photo-sensing element PD may be transmitted to the data line DLj via the pixel switch PS as turned on. In this connection, the data capacitor Cd is charged with the pixel signal.

The amplification unit 121 amplifies the pixel signal. That is, the output of the amplifier AMP outputs the second association signal corresponding to the amplified pixel signal. Further, since the output of the amplification unit 121 already includes the offset of the amplifier AMP, the second association signal includes the amplified pixel signal and the offset of the amplifier AMP. Thus, the second association signal includes the output signal of the photo-sensing element PD, the offset of the pixel region P, and the offset of the amplifier AMP.

Then, as shown in FIG. 9, when the second buffer switch SWb2 is turned on during the third period P3 of the detection period DP, the second association signal is transmitted to the second buffer capacitor Cb2 through the second buffer switch SWb2 that is turned on. Thus, the second buffer capacitor Cb2 is charged with the second association signal.

Thus, the first, second, and third buffer capacitors Cb1, Cb2, and Cb3 are charged with the first, second, and third association signals, respectively.

Then, the multiplexer 123 derives the sensing signal of each pixel region P based on the first, second and third association signals from the first, second and third buffer capacitors Cb1, Cb2 and Cb3.

That is, the multiplexer 123 derives the sensing signal of each pixel region P by subtracting the first and third association signals from the second association signal. In this connection, the sensing signal of each pixel region P does not include the offset of the amplification unit 121 and the offset of the pixel region P and thus may be substantially equal to the output signal of each photo-sensing element PD. This may improve the accuracy of the sensing signal.

When the X-ray image is generated based on the sensing signal of each pixel region P, the effect of the offset of the device 100 itself on the X-ray image may be reduced. Therefore, the accuracy and reliability of the X-ray image as produced by the digital X-ray detector 100 may be improved.

Further, according to an aspect of the present disclosure, the process of transferring the third association signal corresponding to the offset of the pixel region to the third buffer capacitor Cb3 (paths ① and ② in FIG. 5) may be implemented during the portion (PIP in FIG. 4) of the idle period IP prior to the radiation period XRP. Accordingly, since the third association signal corresponding to the offset of the pixel region is derived, there is an advantage that the detection period DP after the radiation period XRP may be prevented from being increased.

However, since the amplification unit 121 and the signal buffering unit 122 correspond to each data line DL, the third association signal transmitted to the third buffer capacitor Cb3 during the portion (PIP in FIG. 4) of the idle period IP prior to the radiation period XRP corresponds to the offset of at least one pixel region P as selected randomly. That is, the third association signal transmitted to the third buffer capacitor Cb3 does not correspond to the offset of each pixel region P.

Therefore, there is a problem that an error between the sensing signal of each pixel region P derived by the multiplexer 123 and the output signal of the photo-sensing element PD of each pixel region P may become large.

Accordingly, a driving method of the digital X-ray detector 100 according to another aspect of the present disclosure is provided as follows.

Figure 10:
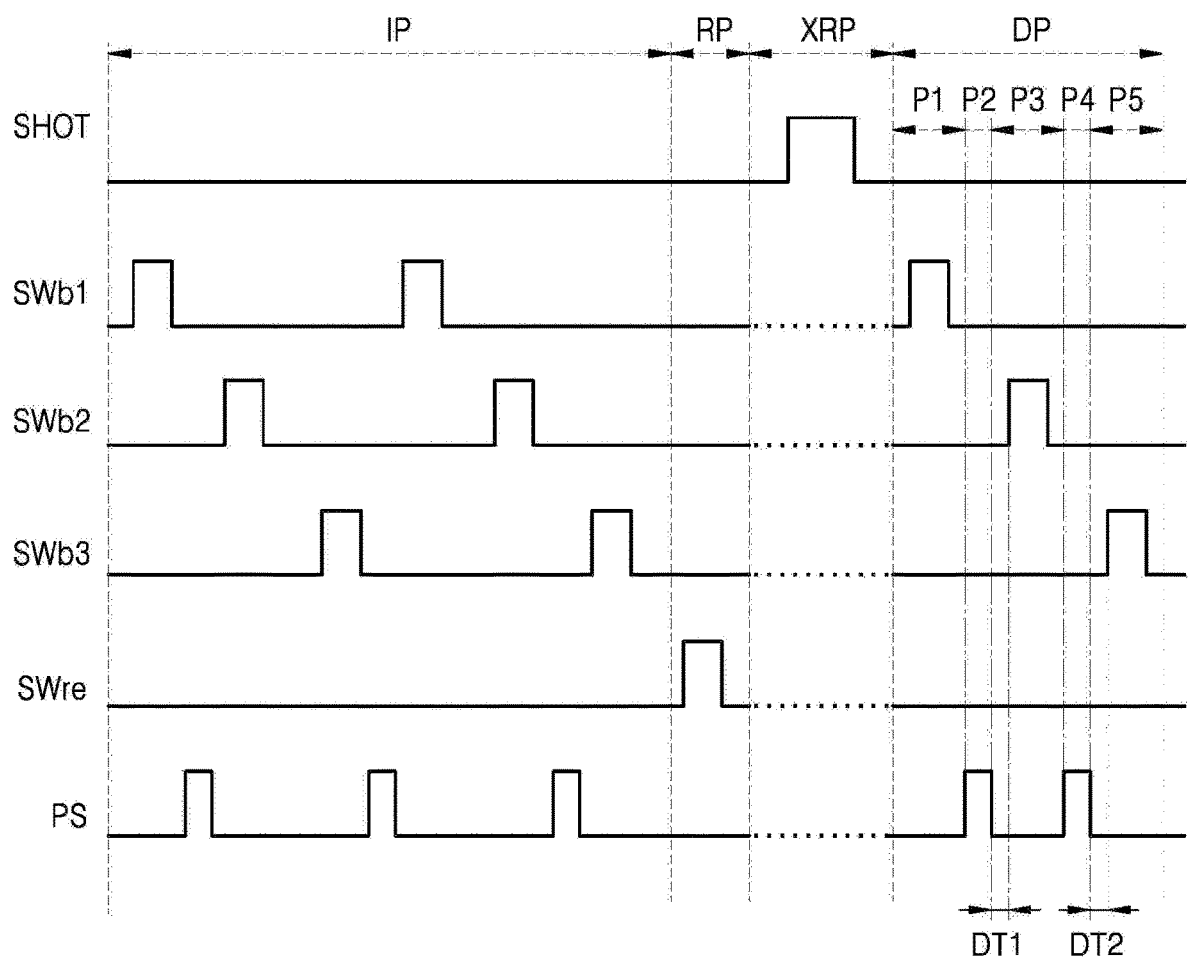
FIG. 10 is a diagram showing a driving waveform corresponding to the pixel region and the read-out driver of FIG. 3 according to another aspect of the present disclosure.

FIG. 10 is a diagram showing a driving waveform corresponding to the pixel region and the read-out driver of FIG. 3 according to another aspect of the present disclosure.

As shown in FIG. 10, the driving method of the digital X-ray detector 100 according to another aspect of the present disclosure may be the same as that of the aspect of the present disclosure shown in FIG. 4, except that the first, second and third buffer switches SWb1, SWb2, and SWb3 and the pixel switch PS are alternately turned on and off during the idle period IP, and the third association signal corresponding to the offset of the pixel region P is transmitted to the third buffer capacitor Cb3 not during the portion (PIP in FIG. 4) of the idle period IP but during a fourth period P4 and a fifth period P5 after the third period P3 of the detection period DP. Thus, redundant descriptions therebetween will be omitted below.

According to another aspect of the present disclosure, during the idle period IP, the first, second, and third buffer switches SWb1, SWb2, and SWb3 and the pixel switch PS are alternately turned on and off. In this connection, the number of times the first, second and third buffer switches SWb1, SWb2, and SWb3 and the pixel switch PS are turned on may be at least one.

During the idle period IP, the pixel switches PS of all of the pixel regions P may be turned on and off at the same time. Alternatively, during the idle period IP, the pixel switches PS of at least one horizontal line may be turned on and off sequentially.

Then, during the reset period RP after the end of the idle period IP and just before the radiation period XRP, the reset switch SWre turns on.

During the radiation period XRP, emission SHOT of the X-ray to the pixel array 110 is performed.

Next, according to another aspect of the present disclosure, the detection period DP after the radiation period XRP includes the first, second, third, fourth and fifth periods P1, P2, P3, P4 and P5.

During the first period P1 of the detection period DP, the first buffer switch SWb1 is turned on.

In this connection, as shown in FIG. 7, when the first buffer switch SWb1 is turned on during the first period P1 of the detection period DP, the first association signal corresponding to the offset of the amplifier 121 is transmitted to the first buffer capacitor Cb1 through the first buffer switch SWb1 that is turned on. In this connection, the first association signal includes the output of the amplifier AMP irrespective of the signal of the data line DLj.

During the second period P2 of the detection period PD, the pixel switch PS is first turned on.

In this connection, as shown in FIG. 8, when the pixel switch PS is turned on during the second period P2 of the detection period DP, the pixel signal including the offset of the pixel region P and the output signal of the photo-sensing element PD may be transmitted to the data line DLj via the pixel switch PS as turned on.

The amplifier AMP amplifies the pixel signal, and outputs the second association signal including the amplified pixel signal and the offset of the amplifier AMP. In this connection, the second association signal includes the output signal of the photo-sensing element PD, the offset of the pixel region P, and the offset of the amplifier AMP.

During the third period P3 of the detection period PD, the second buffer switch SWb2 is turned on.

In this connection, as shown in FIG. 9, when the second buffer switch SWb2 is turned on during the third period P3 of the detection period DP, the second association signal is transmitted to the second buffer capacitor Cb2 through the second buffer switch SWb2 that is turned on.

Next, a second turn-on operation of the pixel switch PS is performed during the fourth period P4 of the detection period PD.

In this connection, as shown in the first path ① in FIG. 5, the pixel offset signal including the offset of each pixel region P is transmitted to the data line DLj through the pixel switch PS as turned on. Further, the data capacitor Cd is charged with the pixel offset signal.

The amplifier AMP outputs the third association signal corresponding to the pixel offset signal.

Then, during the fifth period P5 of the detection period PD, the third buffer switch SWb3 is turned on.

In this connection, as shown in the second path ② of FIG. 5, the third association signal corresponding to the pixel offset signal is transmitted to the third buffer capacitor Cb3 via the third buffer switch SWb3 which has been turned on, Thus, the third buffer capacitor Cb3 is charged with the third association signal.

In this connection, since the third association signal is to remove the offset of the pixel region P from the second association signal, the third association signal needs to correspond to the offset of the pixel region P before the second association signal is generated.

To this end, a length of a period corresponding to the third association signal, that is, a duration from a time point of the first turn off of the pixel switch PS to a time point of the second turn on of the pixel switch PS, that is, the third period P3 is equal to a length of an elapsed period from the end time point of the irradiation of the X-ray to a time point of the first turn on of the pixel switch PS, that is, the first period P1. In this way, the third association signal may be more substantially identical to the offset of the pixel region P included in the second association signal.

A first delay period DT1 in the third period P3 from the time point when the pixel switch PS is first turned off, that is, the end point of the second period P2 to the time point when the second buffer switch SWb2 is first turned on may be equal to a second delay period DT2 in the fifth period P5 from a time point when the pixel switch PS is second turned off, that is, the end time of the fourth period P4 to a time point when the third buffer switch SWb3 is first turned on. Thus, the third association signal may correspond to the offset of the amplifier AMP similar to the second association signal. As a result, the error between the third association signal and the offset of the pixel region P due to the offset of the amplifier AMP included in the third association signal may be reduced.

Further, the detection period DP is performed on each horizontal line basis. Thus, the third association signal transmitted to the third buffer capacitor Cb3 corresponds to the offset of each pixel region P.

Therefore, the error between the sensing signal of each pixel region P derived by the multiplexer 123 and the output signal of the photo-sensing element PD of each pixel region P may be reduced. Therefore, the accuracy of the sensing signal may be further improved.

Generating the X-ray image based on the sensing signal of each pixel region P may allow the accuracy and reliability of the X-ray image to be further improved.

The present disclosure as described above is not limited to the above-described aspect and the accompanying drawings. It will be apparent to those skilled in the art that various changes, substitutions, and alterations without departing from the spirit and scope of the present disclosure will be apparent to those skilled in the art to which the present disclosure pertains.

What is claimed is:
1. A digital X-ray detector comprising:
   a pixel array including a plurality of pixel regions arranged in a matrix form in a sensing region and a data line and a bias line corresponding to the plurality of pixel regions;
   a photo-sensing element sensing light disposed in each pixel region;

a pixel switch disposed between the photo-sensing element and the data line disposed in each pixel region; and a read-out driver comprising an amplification unit connected to the data line, a signal buffering unit connected to an output of the amplification unit and a multiplexer connected to the signal buffering unit to receive first, second and third association signals and synthesizing a single output signal, wherein the signal buffering unit includes first, second and third buffer capacitors respectively charging the first, second third association signals, wherein the first association signal includes an offset of the amplification unit, the second association signal includes an output signal of the photo-sensing element, and the third association signal includes an offset of the pixel region, and wherein the multiplexer is directly connected to the first, second and the third buffer capacitors and subtracts the offset of the amplification unit and the offset of the pixel region from the output signal of the photo-sensing element.

2. The digital X-ray detector of claim 1, wherein the multiplexer derives the subtraction result as a sensing signal of each pixel region.

3. The digital X-ray detector of claim 1, wherein the signal buffering unit further includes:
a first buffer switch disposed between the amplification unit and the first buffer capacitor.

4. The digital X-ray detector of claim 3, wherein the signal buffering unit further includes:
a second buffer switch disposed between the amplification unit and the second buffer capacitor.

5. The digital X-ray detector of claim 4, wherein the signal buffering unit further includes:
a third buffer switch disposed between the amplification unit and the third buffer capacitor.

6. The digital X-ray detector of claim 3, wherein, during a portion of an idle period prior to irradiation of X-ray to the plurality of pixel regions, the pixel switch is turned on and off, and the third buffer switch is turned on,
wherein a pixel offset signal including the offset of the pixel region is transmitted to the data line via the turned on pixel switch,
wherein the third association signal corresponding to the pixel offset signal is transmitted to the third buffer capacitor via the turned on third buffer switch.

7. The digital X-ray detector of claim 6, wherein, during a detection period after the X-ray irradiation to the plurality of pixel regions, the first buffer switch is turned on, such that the first association signal is transmitted to the first buffer capacitor via the first buffer switch as turned on,
after the first buffer switch is turned off, the pixel switch is turned on, such that a pixel signal including the offset of the pixel region and the output signal of the photo-sensing element is transmitted to the data line via the turned on pixel switch,
after the pixel switch is turned off, the second buffer switch is turned on, such that the second association signal including the pixel signal and the offset of the amplification unit is transmitted to the second buffer capacitor via the turned on second buffer switch.

8. The digital X-ray detector of claim 3, wherein during a detection period after the X-ray irradiation to the plurality of pixel regions, the first buffer switch is turned on, such that the first association signal is transmitted to the first buffer capacitor via the turned on first buffer switch, after the first buffer switch is turned off, the pixel switch is first turned on, such that the pixel signal including the offset of the pixel region and the output signal of the photo-sensing element is transmitted to the data line via the turned on pixel switch, after the pixel switch is first turned off, the second buffer switch is turned on, such that the second association signal including the pixel signal and the offset of the amplification unit is transmitted to the second buffer capacitor via the turned on second buffer switch, after the second buffer switch is turned off, the pixel switch is second turned on, such that a pixel offset signal including the offset of the pixel region is transmitted to the data line via the turned on pixel switch, after the pixel switch is second turned off, the third buffer switch is turned on, such that the third association signal corresponding to the pixel offset signal is transmitted to the third buffer capacitor via the turned on third buffer switch.

9. The digital X-ray detector of claim 8, wherein a length of an elapsed time from a time point when the pixel switch is first turned off to a time point when the pixel switch is second turned on is equal to a length of an elapsed time from a time point when the X-ray irradiation to the plurality of pixel regions terminates to a time point when the pixel switch is first turned on.

10. The digital X-ray detector of claim 1, wherein the amplification unit includes:
an amplifier including a first input connected to the data line and a second input receiving a predetermined reference signal; and
a feedback capacitor disposed between the first input and an output of the amplifier.

11. The digital X-ray detector of claim 1, wherein the multiplexer combines sensing signals of the pixel regions to generate an analog output signal,
wherein the read-out driver further includes a signal converter converting the analog output signal into a digital output signal and a data processing unit generating an image signal based on the digital output signal.

12. A method for operating a digital X-ray detector, wherein the digital X-ray detector includes a pixel array including a plurality of pixel regions arranged in a matrix in a sensing region and a data line and a bias line corresponding to each vertical line composed of pixel regions arranged; and a read-out driver connected to the data line; a photo-sensing element for sensing light disposed in each pixel region; a pixel switch disposed between the photo-sensing element and the data line disposed in each pixel region, and wherein the read-out driver includes an amplification unit coupled to each data line; first, second, and third buffer capacitors coupled to an output of the amplification unit; first, second, and third buffer switches disposed between the first, second, and third buffer capacitors and the output of the amplification unit respectively; and a multiplexer directly connected to the first, second, and third buffer capacitors, the method comprising:
turning on the first buffer switch during a first period of a detection period after irradiating X-ray to the plurality of pixel regions;
turning on the pixel switch during a second period of the detection period;
turning on the second buffer switch during a third period of the detection period; and by the multiplexer, subtracting the offset of the amplification unit and the offset of the pixel region from the output signal of the photo-sensing element.

13. The method of claim 12, wherein a first association signal corresponding to the offset of the amplification unit is transmitted to the first buffer capacitor via the turned on first buffer switch when the first buffer switch is turned on.

14. The method of claim 13, wherein the method further comprises turning on and off the pixel switch and turning on the third buffer switch during a portion of an idle period prior to irradiation of X-ray to the plurality of pixel regions,
wherein during the portion of the idle period, a pixel offset signal including the offset of the pixel region is transmitted to the data line via the turned on pixel switch, and
wherein during the portion of the idle period, a third association signal corresponding to the pixel offset signal is transmitted to the third buffer capacitor via the turned on third buffer switch.

15. The method of claim 14, wherein when the multiplexer derives the sensing signal of each pixel region, the multiplexer substrates the first and third association signals from the second association signal to obtain a subtraction result and the multiplexer derives the subtraction result as the sensing signal.

16. The method of claim 13, wherein the method further comprises:
during a fourth period of the detection period after the third period, turning on the pixel switch such that the third association signal corresponding to an offset of the pixel region is transmitted to the data line via the turned on pixel switch; and
during a fifth period of the detection period after the fourth period, turning on the third buffer switch such that the third associated signal is transmitted to the third buffer capacitor via the turned on third buffer switch.

17. The method of claim 16, wherein a length of the third period is equal to a length of the first period.

18. The method of claim 16, wherein the multiplexer substrates the first and third association signals from the second association signal to obtain a subtraction result and the multiplexer derives the subtraction result as the sensing signal when the multiplexer derives the sensing signal of each pixel region.

19. The method of claim 12, wherein a pixel signal including an offset of the pixel region and an output signal of the photo-sensing element are transmitted to the data line via the turned on pixel switch when the pixel switch is turned on.

20. The method of claim 19, wherein a second association signal including the pixel signal and the offset of the amplification unit are transmitted to the second buffer capacitor via the turned on second buffer switch when the second buffer switch is turned on.

21. A digital X-ray detector comprising:
a pixel array including a plurality of pixel regions arranged in a matrix form in a sensing region and a data line corresponding to the plurality of pixel regions;
a pixel switch disposed between the photo-sensing element and the data line disposed in each pixel region; and
a read-out driver connected to the data line,
wherein the pixel array include a scintillator layer that converts the X-ray to visible light,
wherein the photo-sensing element PD absorbs the visible light from the scintillator layer and generates electrons in response to the visible light, thereby to generate an output signal corresponding to the transmission of the X-ray,
wherein the read-out driver includes:
first and second buffer switches alternately turned on and off with the pixel switch during an idle period prior to a radiation period for irradiating the X-ray to the plurality of pixel regions;
an amplification unit connected to each data line;
a first association signal detector connected to an output of the amplification unit and detecting a first association signal corresponding to an offset of the amplification unit;
a second association signal detector connected to the output of the amplification unit and detecting a second association signal including an output signal of the photo-sensing element;
a third association signal detector connected to the output of the amplification unit and detecting a third association signal corresponding to an offset of the pixel region; and
a multiplexer deriving a sensing signal of each pixel region based on the first, second and third association signals.

22. A method for operating a digital X-ray detector, wherein the digital X-ray detector includes a pixel array including a plurality of pixel regions arranged in a matrix in a sensing region and a data line corresponding to each vertical line composed of pixel regions arranged; and a read-out driver connected to the data line; a photo-sensing element for sensing light disposed in each pixel region; a pixel switch disposed between the photo-sensing element and the data line disposed in each pixel region, wherein the pixel array include a scintillator layer that converts the X-ray to visible light, wherein the photo-sensing element PD absorbs the visible light from the scintillator layer and generates electrons in response to the visible light, thereby to generate an output signal corresponding to the transmission of the X-ray, wherein the read-out driver includes an amplification unit coupled to each data line; first, second, and third buffer capacitors coupled to an output of the amplification unit; first, second, and third buffer switches disposed between the first, second, and third buffer capacitors and the output of the amplification unit respectively; and a multiplexer connected to the first, second, and third buffer capacitors, and wherein the first and second buffer switches and the pixel switch are alternately turned on and off during an idle period prior to a radiation period for irradiating the X-ray to the plurality of pixel regions, the method comprising:
turning on the first buffer switch during a first period of a detection period after irradiating X-ray to the plurality of pixel regions;
turning on the pixel switch during a second period of the detection period;
turning on the second buffer switch during a third period of the detection period; and
deriving, by the multiplexer, a sensing signal of each pixel region, based on first, second and third association signals corresponding to the first, second and third buffer capacitors respectively.

* * * * *